United States Patent [19]

Southworth

[11] 4,136,680
[45] Jan. 30, 1979

[54] SELF-CONTAINED APPARATUS FOR COLLECTION AND MAINTENANCE OF MEDICAL SPECIMEN AND METHODS OF USING SAME

[75] Inventor: Anna M. Southworth, San Diego, Calif.

[73] Assignee: Transmed Corp., San Diego, Calif.

[21] Appl. No.: 692,826

[22] Filed: Jun. 4, 1976

[51] Int. Cl.² ............................................. A61B 10/00
[52] U.S. Cl. .................................. 128/213; 128/2 W; 195/103.5 R
[58] Field of Search .............. 128/2 B, 2 W, 304, 269, 128/2 R; 195/103, 5 R, 127; 73/425.2, 425.4 R, 425.4 P

[56] References Cited

U.S. PATENT DOCUMENTS

| 3,037,496 | 6/1962 | Melges | 128/2 W |
|---|---|---|---|
| 3,308,039 | 3/1967 | Nelson | 128/2 W X |
| 3,438,366 | 4/1969 | Kariher et al. | 128/2 B |
| 3,513,830 | 5/1970 | Kalayjian | 128/2 W |
| 3,651,926 | 3/1972 | Elfast | 128/2 B |
| 3,773,035 | 11/1973 | Aronoff et al. | 128/2 W |
| 3,877,464 | 4/1975 | Vermes | 128/2 B |
| 3,890,204 | 6/1975 | Avery | 128/2 W X |
| 3,913,564 | 10/1976 | Freshley | 128/2 W |
| 3,939,044 | 2/1976 | Wilkins et al. | 128/2 W X |
| 3,952,729 | 4/1976 | Libman et al. | 128/2 F |

Primary Examiner—Robert W. Michell
Assistant Examiner—Michael H. Thaler
Attorney, Agent, or Firm—William F. Frank

[57] ABSTRACT

A specimen collecting apparatus, with variations, providing for all, or part, or combinations of the following:

Self-contained in-line transport and culture container that maintains the sealed state of its chamber within, before, during, and after the entry of the collected specimen.

Aerobic or anaerobic swab devices, with swab rods of varying lengths and curvatures.

Removable protective tubes for taking specimen from its existing environment, directly to sealed chamber without passing specimen thru ambient air.

Self-contained transport media.

Self-contained culture media and means for inoculating specimen on said media within said chamber for direct placement in incubators.

Self opening protective tips for contamination protection during insertion and withdrawal from specimen locations.

All parts, integratable for an assembly for collecting and maintaining specimen, and the method of operation of same.

47 Claims, 25 Drawing Figures

U.S. Patent Jan. 30, 1979 4,136,680
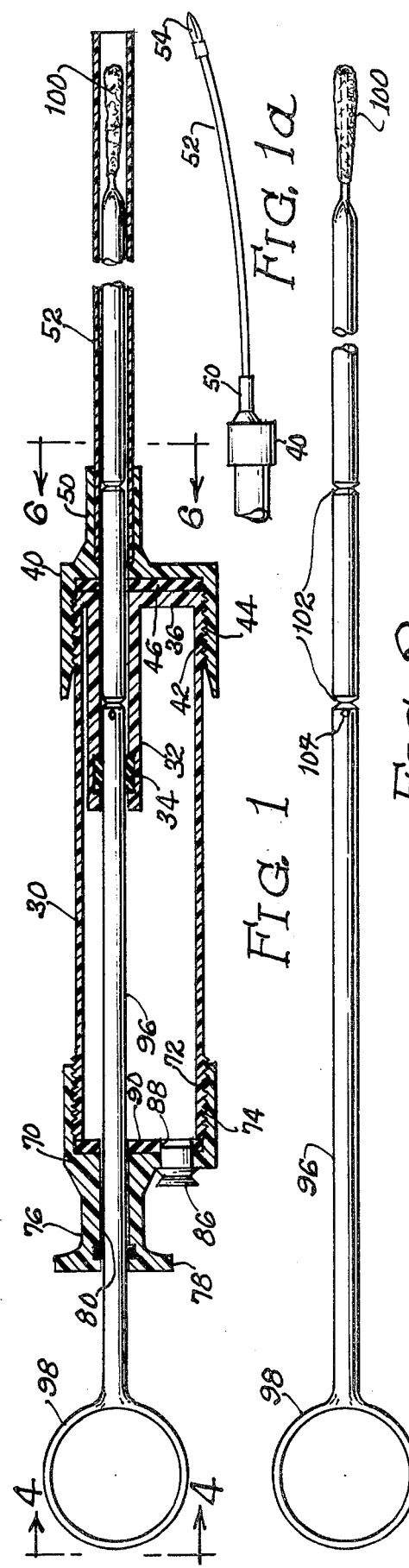
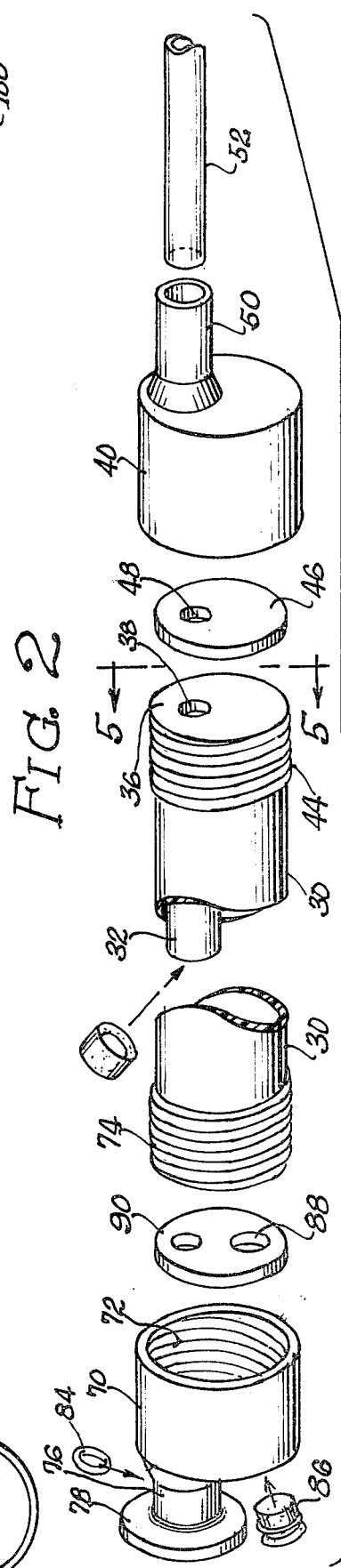
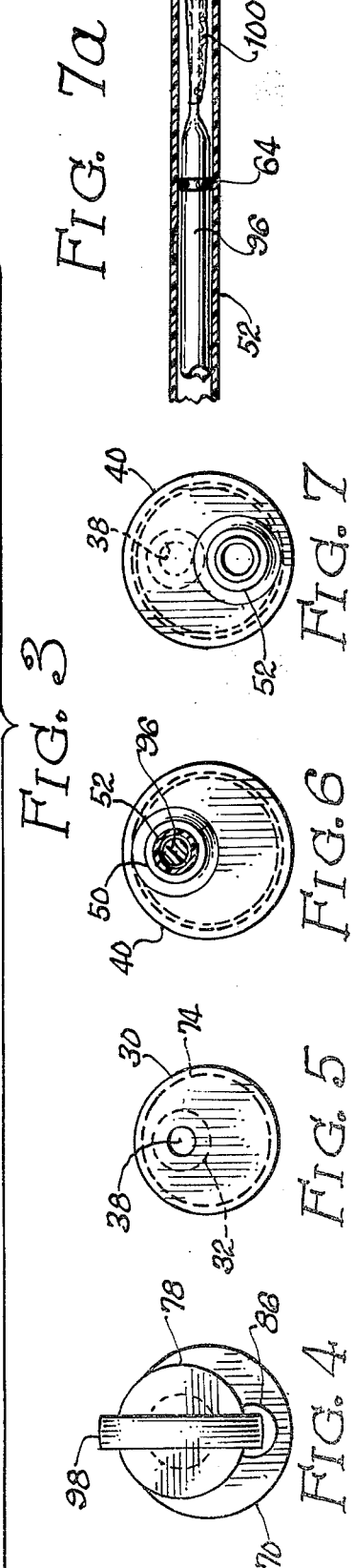

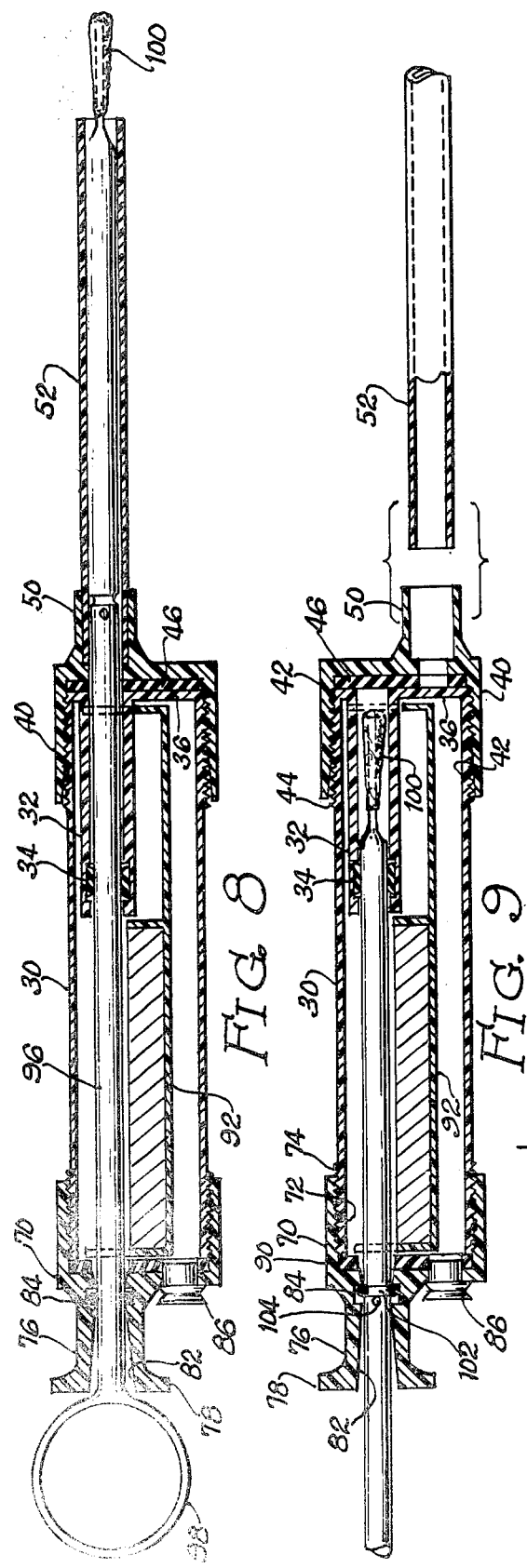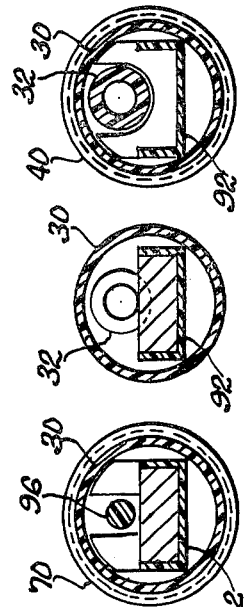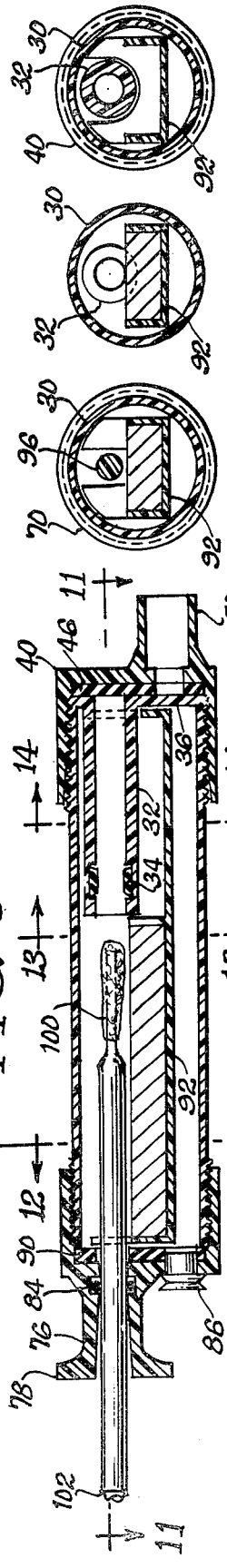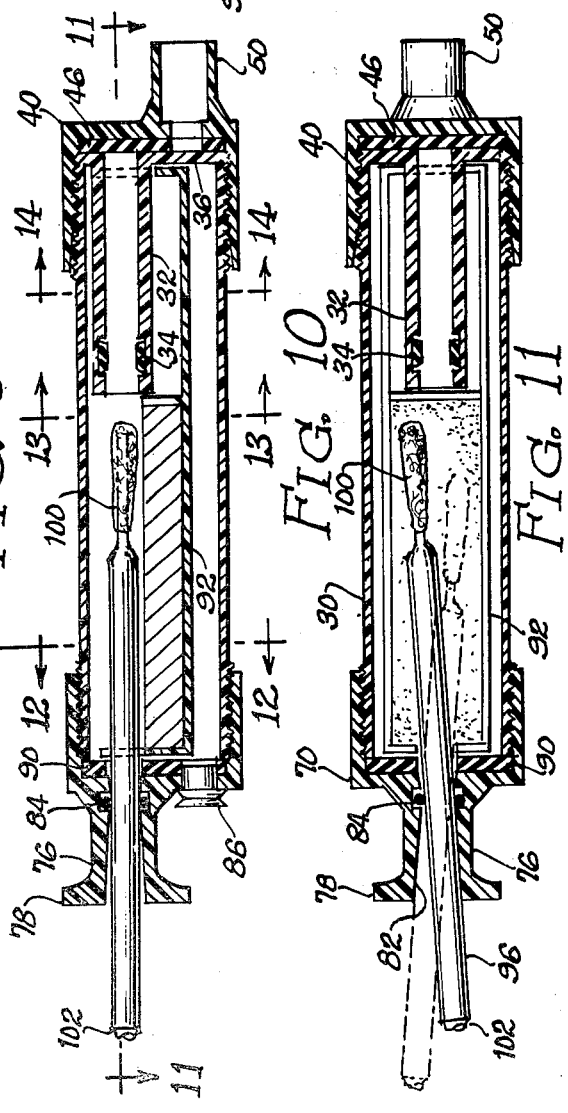

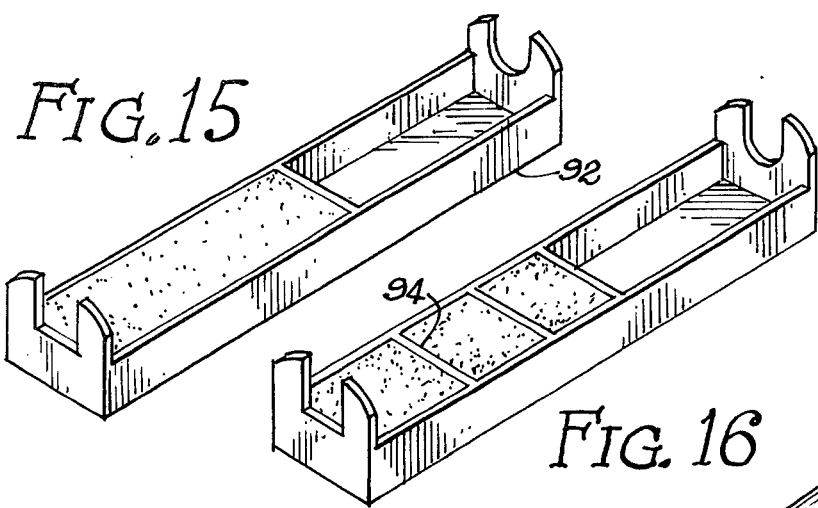
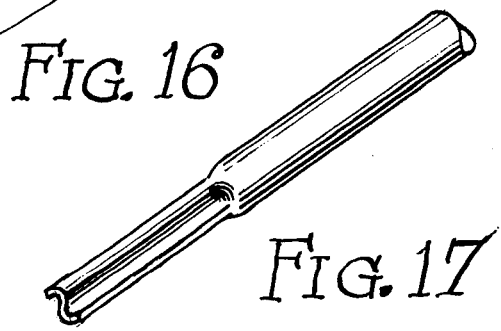
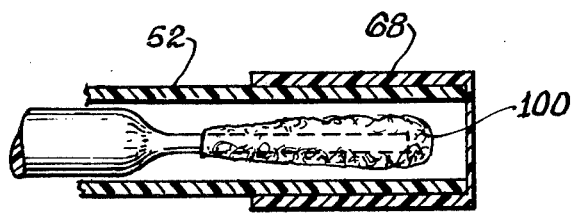
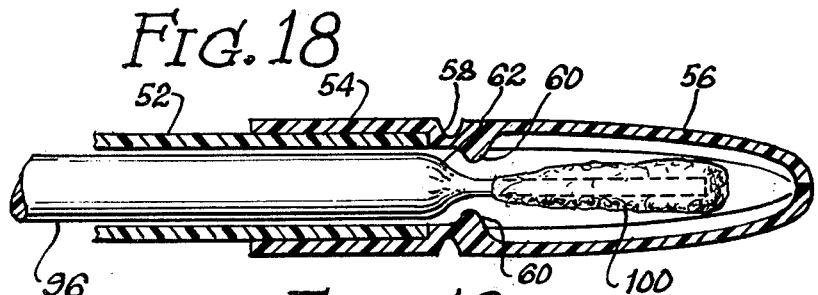
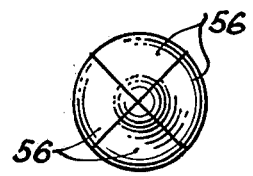
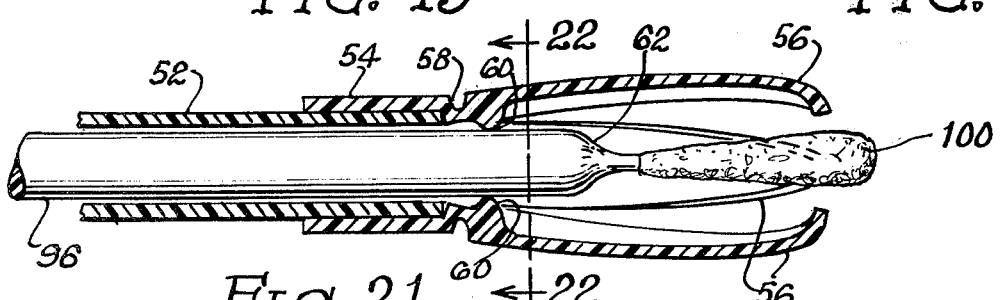
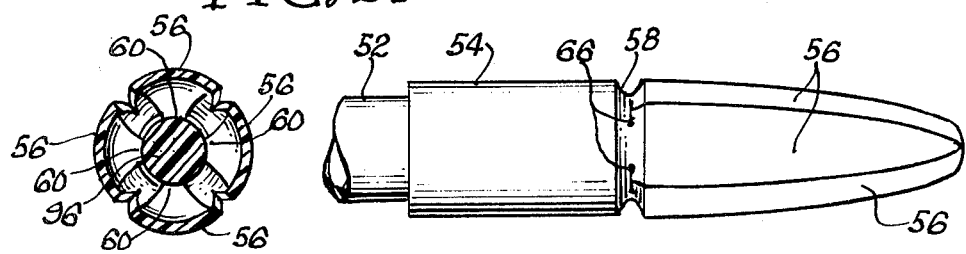

SELF-CONTAINED APPARATUS FOR COLLECTION AND MAINTENANCE OF MEDICAL SPECIMEN AND METHODS OF USING SAME

BACKGROUND OF THE INVENTION

The present invention relates generally to swab devices and methods for using same to obtain bacteriologic or microbiologic specimens.

The gathering of bacteriologic specimen for culture is a complex subject and not well suited for simplification, but listed below are some generally accepted facts:

There is a wide variety of methods for collecting specimen for culture, and unfortunately no one method can best be applied for the recovery of all infectious agents.

Some bacterium is very sensitive to sudden changes in temperature.

Exposure of the microorganisms to small quantities of oxygen may kill or severely injure fastidious anaerobes.

Prolonged exposure to atmosphere has a drying effect that is detrimental to bacteriologic specimens.

In general, the handling of the specimen from point of collection to proper analysis in the laboratory is vitally important.

Present art standard anaerobic swabs, most commonly used today for collecting anaerobes, have their shortcomings:

Their pre-use anaerobic state is compromised when containers are uncapped and there is an admission of some air into previously oxygen free containers. Swab members are passed thru air enroute to bacteria location, and swab and specimen are passed thru air while being taken back to said oxygen free transportation container. Because it is imperative that these swab devices be held upright, they are less than convenient and subject to faulty handling practices.

Presently, once specimen arrives at laboratory, specimen sometimes sits before specimen is inoculated on proper selective culture medias. Once laboratory process begins, anaerobic specimens are again introduced into air when transport containers are opened and specimen is inoculated on culture media and taken to incubators.

Recent inventions, that create their own anaerobic atmosphere through the use of ampules, capsules granules, filters, puncturing pressurized $CO_2$ cylinders and the like, cam sometimes be complicatedly impractical, economically unreasonable, and less than optimum efficient. In all cases they pass the specimen thru air during their use.

SUMMARY

The present invention provides a device for the convenient collection and preservation of bacteriologic or microbiologic or tissue specimen. With it, one can gather specimen from its original environment and take such specimen directly to its proper transport and or culture media without passing same through air. This is accomplished by a self contained, in-line sealed chamber into which a swab rod can be brought without loss of seal. Such rods and their protective tubes vary in length to accommodate their various use. Not uncommonly bacteria exist in locations difficult to reach, as in body cavities, such as cervical and uterus areas. The sealed chamber can easily and inexpensively be prefilled with precise desired transport and or culture media, may they be gaseous, liquid, solid, gelatinous or combinations thereof.

This invention is readily adaptable to a variety of uses so that by virtue of a great number of units being manufactured, it will be economically feasible for it to create some standardization of various devices and techniques for their use.

This versatile contribution to the art includes four basic related, but different, combinations of parts for use in various situations. More specifically, there's a body portion and specimen collecting means only, for use in those instances in which the specimen is readily accessible. Next, a swab protective tube may be added to avoid contamination of the swab as it travels to the area of collection and returns. The otherwise open end of the tube may, if desired, be provided with a protective tip or cap. This completely closes the system, except when the swab emerges to take a specimen. Thereby keeping swab free of contamination during insertion and withdrawal process. And lastly, various culture media may be positioned within the body portion for direct maintenance in a closed, controlled system. Therefore specimen can be taken from bacteria location, be inoculated on proper selective culture media, and be put into incubator without ever being passed through room atmosphere. These and other and further objects and advantages of the present invention will become readily apparent from the following descriptions and the accompanying drawings.

BRIEF DESCRIPTION OF THE DRAWINGS

FIG. 1 is a longitudinal sectional view of the invention.

FIG. 1a is a perspective view of the swab rod protective tube portion of the device.

FIG. 2 is a side elevation of the swab rod.

FIG. 3 is a perspective exploded view of the entire assembly, except the end of the protective tube and swab rod.

FIG. 4 is an end view taken along lines 4—4 of FIG. 1.

FIG. 5 is an end view taken along lines 5—5 of FIG. 3.

FIG. 6 is a cross sectional end view taken along lines 6—6 of FIG. 1.

FIG. 7 is a cross sectional end view showing as the device would appear along line 6—6 if the swab end body cap were rotated to a closed position.

FIG. 7a is an alternate form with an O-ring on the rod member.

FIG. 8 is a longitudinal sectional view of the device with cultural media tray and with swab rod extended.

FIG. 9 is the same as FIG. 8 but with the end of the rod retracted into the chamber seal tube.

FIG. 10 is the same as FIG. 8 but with the rod end fully retracted into the body portion.

FIG. 11 is a top plan view of the same form of the device showing the swab inoculating culture media.

FIG. 12 is a cross sectional view taken along line 12—12 of FIG. 10.

FIG. 13 is a cross sectional view taken along line 13—13 of FIG. 10.

FIG. 14 is a cross sectional view taken along line 14—14 of FIG. 10.

FIG. 15 is a perspective view of a culture media tray that may be positioned within the body portion.

FIG. 16 is a perspective view of a modification of said tray having multiple compartments.

FIG. 17 is a perspective view of a blade specimen collector end of rod member.

FIG. 18 is a sectional detail of the end of the swab protective tube with swab and cap.

FIG. 19 is a cross sectional detailed view of the end of the closed swab protective tube and its conical section cover with swab enclosed.

FIG. 20 is a view from the end thereof.

FIG. 21 is the same as FIG. 19 with the swab partially extending from the tube and opened conical section.

FIG. 22 is a cross sectional view taken along line 22—22 of FIG. 21.

FIG. 23 is a longitudinal view of the closed swab protective tip.

DESCRIPTION OF THE PREFERRED EMBODIMENTS

Referring to the drawings wherein like numerals represent like parts throughout, the numeral 30 represents a body assembly or portion being, preferably, an elongated cylindrical member in configuration and formed of disposable plastic. It is closed at its end nearest the swab, except for a small orifice through which rod member passes. Within item 30 is an integral sealable enclosure 32, being mounted, excentrically to and at one end of the body portion as illustrated. To provide greater surface area for specimen media item 30 may be a rectangular cube.

An important feature of my novel arrangement of parts is the facility for controlling, at all times, the environment into which the bacteria specimens are exposed. Seals between chambers, forming an air-lock type sealed zone, permit this desired result. The assembly is a sealed chamber means having a hollow sealing member extending inwardly from one end. O-ring seal 34 is seated into a recess around the inside perimeter of enclosure 32. It serves as both annular seal and bearing surface. It is expected this form of the device having the O-ring seal will be used only in connection with a liquid media in the outer chamber. A modified form is shown in FIG. 7a wherein one or more O-rings 64 are mounted in a groove or grooves annularly around the rod for snug fitting in the protective tube and enclosure 32 in place and instead of described stationary O-rings. The opposite closed end of enclosure 32 is designated by the numeral 36, and is best seen in FIG. 3. It is provided with portal 38 through which the later described swab rod slides.

My novel cap 40 covers the body portion at the end nearest the swab. It is of the usual cup configuration on one end and a sleeve like projection 50 on the other end. Within the cup are threads 42 for engagement with threads 44 on the outside of one end of the body. To insure sealing, there is a cap liner or gasket 46 being a disk that fits between the inside of the cap and end of the body. It also has an orifice 48 to accept the swab rod when aligned for that purpose. The orifice is in sealing relationship with the swab rod. The foregoing constitutes the sealing means. Other routine sealing means could be employed.

Continuing with parts outside the body portion next in order I have provided protective tube 52. It may be straight or curved and made of same plastic as the body portion. Its outside diameter is preferably slightly smaller than the inside diameter of projecting sleeve 50 for a telescoping snug friction fit while in use, and for easy removal for disposal before or after use. Reduced FIG. 1a shows it in place for use. Its length is suitable for reaching organ or tissue within the human body. It serves as a guide for the swab rod as well as a shield for the swab. The fact that the tube is removable is an important feature of the novel assembly. Where the specimen to be taken is readily accessible without opportunity of contaminating the swab in reaching it, the tube can be removed before using. In other instances, it is removed after the swab is retracted into the body portion for convenience of handling.

To further expedite uncontaminated sampling, a remotely controlled protective cap 54 covers the end of tube 52 opposite that attached to the body portion. It has a plurality of expandable conical sections 56 integral with a cylindrical section that friction fits over the end of tube 52. For illustration, reference is made to FIG. 19 and subsequent. As can be seen, an exterior groove 58 circumvents the cap to facilitate hinging of the conical sections. Oppositely disposed thereto, within the inside of the unit are a plurality of spurs 60 which are contacted by shoulders 62, being the area of size change of the swab rod. Responding to the lines of least resistance sections 56 expand into an open position as in response to the cam-follower action when the swab rod member 96 is moved in respect to tube 52. Spurs 60 are not continuous, but rather, have space between them to minimize loss of specimen by scraping. The transverse dimension of the rod is reduced at the swab portion. This too avoids loss of specimen on walls of protective tube. Also, a plurality of horizontal cuts 66 through the cap in the base of groove 58 weaken the area for controlled hinge action. "Memory" of the sections cause them to again close when the swab, now with specimen, is retracted into the tube. Of course, other arrangements may be used to avoid untimely exposure of the swab. For example, the plain cap 68 of FIG. 18 might be used. The material covering its end could be such that it would be easily ruptured by an emerging swab as it is manually forced to protrude from the tube. Also, a plain, non-ruptureable cap may cover, then be removed before use to avoid being in the path of an emerging swab.

Directing attention now to the end of the body portion opposite that of the swab, I have provided a handle end cap 70 of same material as that of the body portion on which it fits by threaded engagement with its inside threads 72 and the outside threads 74 on the end of the body portion. It preferably has a tubular projection 76 with flanged end 78 for use as a finger grip. In that form of my device, not designed for innoculating media within the body, cap 70 has an inner passageway 80 with parallel sides. See FIG. 1. In alternate forms, the passageway has tapered walls 82, opening outward, to permit the rod action shown in FIG. 11. Within both forms is bearing seal 84, preferably being an O-ring seated with a groove in cap 70. Other features of the cap include a removable plug 86 of resilient material which fits into filler means 88 being an orifice that opens into the chamber of the body portion for filling and holding various materials in various physical states, prepared during the manufacture of the device. There is a disk gasket 90 between cap and body. There is an orifice therein for the swab rod to pass through and another orifice therein aligned with filler plug to permit material to pass through.

Turning now to the contents within the body chamber, in certain forms of the invention there are media containers shown in FIGS. 15 and 16. Container 92 is tray-like of rectangular shape with a base, closed ends and sides and an open top. It is designed to hold various culture media, such as the various forms of agar. The end closest to the swab has a U-shaped recess to fit around enclosure 32. One or more partitions 94 may be provided to separate the space into which the media is placed into compartments. This would permit concurrent inoculation of more than one media.

To complete the parts of the device, attention is now directed to movable specimen collecting means or swab member 96. It is perhaps best depicted in FIG. 2. As illustrated it is a rod with a thumb ring handle 98, for easy gripping, at one end and a swab 100 at the other. The rod is preferably made of plastic. The swab itself is preferably made of absorbent material, other than cotton, such as rayon or dacron. For use in collecting tissue substances, by cutting or scraping, a blade may be affixed to the rod in place and instead of the swab. See FIG. 17. Also, those skilled in the art may use sponges or the like as an alternative to the swab as particular requirements may suggest without department from the scope of my subjoined claims.

There are grooves marked 102 cut around the rod for signalling to the user and as weakened points for controlled breaking promptly after a sample is taken. Pin hole 104 also is through the rod to weaken it at a particular point for breakage.

Of course, variations of the specific construction and arrangement of the device can be made by those skilled in the art without departing from the invention as defined in the appended claims.

To use a described form of the device, the technician places the swab end of the tube 52 next to the part of the human body having the bacteria to be sampled. Typically, tube 52 would be inserted into a vagina with section 56 next to the cervix of the uterus with parts in the position shown in FIG. 19. The user then holds the body portion 30 steady and pushes the handle 98 forward. This causes the swab to emerge as in FIG. 21. The swab is brought into contact with the human body and the sample taken in the usual manner. Then the motions are reversed and the swab member is retracted into enclosure 32 as shown in FIG. 9. The distance between a groove 102 and the end of the swab is such that the groove seats in O-ring 84 when the swab is within the enclosure 32. The operator feels a minor resistance or "click" in his hand that is retracting the rod. This sensation is a signal to stop the rod movement and, next, to partially rotate cap 40 whereby orifices and passageways through which the swab had just passed are no longer aligned. This operation seals the enclosure 32 and cuts it off from the room atmosphere. Such rotation shifts projection 50 from its position in FIG. 8 to that of FIG. 9. The closure operation just described could be performed before or after removal of the device from the body cavity or specimen location. Tube 52 is now removed and discarded. Next, the rod is further manually drawn into body 30 and the swab is brought into contact with the culture media, inoculating it with "Z" motions, or otherwise, as illustrated in FIGS. 11 and 13. Thereafter the rod is broken at pin hole 104. In the rod form having two annular grooves as shown in FIG. 1, the entry of the second groove into O-ring 84 signals the operator to break off the exterior gripping end of the rod and discard it. After transportation to laboratory, unit can be put directly into incubator, or, be further processed as lab technician may desire. Media tray removal is facilitated by removal of grip end cap. Treatment and examination of contents is in the conventional manner, and the described device is disposed of.

The basic technique described above will vary somewhat according to the form of device chosen for the particular location of specimen and examination to be made. Accordingly, where agar is to be inoculated, the form of cap 70 shown in FIGS. 8 thru 11 is used, and not the form shown in FIG. 1. Only by having tapered walls 82 may the swab be jiggled on the agar, as depicted in FIG. 11. In forms of the device wherein there is only transport media within the chamber of the device, the grip end cap, with specimen bearing swab still attached, will be removed at the laboratory for inoculation of said specimen onto proper culture media and further processing.

This being the first device with facilities for multiple cultural media, one section of the culture tray may contain selective media for general enrichment, such as blood agar; another compartment may concurrently have a selective media for gram negative organisms, such as MacKonky's and a third section may have a selective media for gram positive organisms, such as CNA. By having all media inoculated simultaneously not only are time and effort saved, but circumstances of inoculation are uniform, and therefore not an unwanted variable for comparative tests and studies.

The various combination of parts lend themselves to many special uses. For illustration, a specimen may easily and quickly be placed on a microscope slide by pulling swab rod with specimen completely out of the assembly as assembly is being placed in incubator.

Also, if desired, the form shown in FIGS. 8 thru 10 may have plug 86 removed to allow the chamber to admit the atmosphere of the incubator.

It is expected that some packages or envelopes containing some forms of the device will be in an anaerobic state while others will simply be sterile.

I claim:

1. A self-contained apparatus for collecting bacteriological or microbiological or tissue specimen and maintaining said specimen, comprising: chamber means having two longitudinally opposing end portions, each having sealing means thereon, for containing therein a non-contaminating and non-debilitating specimen maintenance environment for said specimen, a movable specimen collecting means positioned within and passing through said chamber means and each of said sealing means in cooperation with said sealing means to seal said chamber means, said collecting means being extended from one of said end portions to collect said specimen and then retracted with said specimen through said one end portion into said chamber means, and additional sealing means on said one end portion to close and seal said one end portion after said retraction, wherein said additional sealing means is positioned outwardly and longitudinally of the sealing means on said one end portion, and has an open position to cooperate with said one end portion for the collecting of said specimen and a closed position to close and seal said one end portion and said chamber means after said specimen has been retracted into said chamber means.

2. Apparatus according to claim 1 further comprising means within said chamber means to receive and maintain said collected specimen for laboratory analysis.

3. A self-contained apparatus for collecting a bacteriological or microbiological or tissue specimen and maintaining said collected specimen in a sealed, non-contaminating and non-debilitating environment for laboratory analysis comprising:

a body assembly having longitudinally opposing end portions with sealing means on each postion;

specimen collecting means movably positioned within and passing through said body assembly and each said sealing means in sealing relationship therewith to form a sealed interior of said assembly, said collecting means extending from one end portion of said assembly to collect said specimen and retracting into said one end portion with said specimen into said sealed body assembly;

said assembly further having therein said environment consisting of specimen maintenance medium selected from the group of gaseous, liquid, solid, gelatinous media and combinations thereof to receive and maintain said collected specimen after said retraction; and additional means on said one end portion to provide closing and sealing of said one end portion after said retraction of said specimen into said chamber interior, said means being positioned longitudinally and outwardly of said sealing means on said one end portion and having an opening therethrough which has an open position to cooperate with said one end portion for said specimen collection and retraction and a closed position to close and seal said one end portion after said retraction.

4. The apparatus according to claim 3, wherein said additional sealing means comprises a cylindrical cap having a sealing gasket positioned on the interior thereof, an orifice in said gasket communicating with an orifice in the end of said cap in coaxial relationship, said gasket orifice and said cap orifice being so positioned as to be coaxial with said one end orifice and said hollow member orifice.

5. The apparatus according to claim 4, wherein said cap is adapted for additional rotation about the major axis of said body assembly so as to move said gasket and cap orifices out of coaxial alignment with said hollow member said one end orifices to cover said orifice in sealing relationship.

6. The apparatus according to claim 5, wherein a cylindrical sleeve is formed on the outer surface of said cap coaxial with said orifice in said cap, said sleeve having an interior diameter greater than the diameter of said cap, orifice.

7. The apparatus according to claim 6, wherein said sleeve carries a removeable, elongated protective tube, said protective tube being of an interior diameter to receive said specimen collecting means in frictionless fit.

8. The apparatus according to claim 7, wherein a cap is provided for the protective tube end opposite said sleeve.

9. The apparatus according to claim 8, wherein said cap comprises a cylindrical sleeve having a rupturable membrane covering one end of said sleeve.

10. The apparatus according to claim 8, wherein said cap comprises a cylindrical sleeve frictionally fitted over said end of said tube and a closed conical projection extending from said sleeve, said conical projection comprising a plurality of separable segments formed of a resilient material having memory; said segments being in sealing relationship with each other, said segments being adapted to be separated to uncover the end of said tube, and means on the interior of said conical projection adjacent said sleeve to separate said segments when said means is contacted by said specimen collecting means.

11. The apparatus according to claim 10, wherein said segment opening means comprises a plurality of segments arranged in an annular path, the number of annular segments corresponding to the number of conical segments.

12. The apparatus according to claim 4, wherein said gasket orifice is of a diameter to engage said slidable specimen collecting means in sealing relationship therewith to additionally seal the interior of said body assembly.

13. The apparatus according to claim 3, wherein said specimen collecting means has its longitudinal axis of movement parallel to but radially spaced from the longitudinal axis of said assembly to provide a zone for said receiving and maintenance means.

14. The apparatus according to claim 13, wherein said specimen collecting means comprises an elongated slender rod having a specimen collector on one end thereof and gripping means on the opposite end thereof.

15. The apparatus according to claim 14, wherein said rod has a second annular groove formed thereon at a predetermined position on said rod from said collector to indicate the position of said specimen collector within said body assembly after said retraction thereinto.

16. The apparatus according to claim 14, wherein the maximum lateral dimension of said specimen collector is less than the diameter of said rod to protect said specimen during its passage through said first and second sealing means.

17. The apparatus according to claim 14, wherein said specimen collecting means carries an annular ring of resilient material to engage the interior of a protective tube extending from said one end and the interior of said hollow member of said body assembly in sealing relationship therewith.

18. The apparatus according to claim 3, wherein said media is selected from the group of transport and culture media.

19. Apparatus according to claim 18, wherein said medium is at least one culture type carried by a tray inserted into the interior of said body assembly, said tray having means on at least one end to cooperate with the said body assembly to prevent movement of said tray therein.

20. The apparatus according to claim 19 wherein said tray is divided into at least two culture media containing compartments, each compartment containing a different culture type medium.

21. The apparatus according to claim 3 wherein said body assembly comprises a hollow elongated cylindrical member; said one end portion having a hollow member extending therefrom to slidably and sealingly receive said collecting means and an orifice coaxial with said hollow member for said extending and retracting of said collecting means; said opposing end portion having a closure therefor with a passageway therethrough for said collecting means, said passageway being coaxial with said hollow member and said orifice.

22. The apparatus according to claim 21, wherein said passageway in said closure means comprises a cylindrical shape.

23. The apparatus according to claim 22, wherein said passageway comprises a venturi-like opening formed by the intersection of two cones to provide orbital movement of said collecting means within said sealed body after said retraction.

24. The apparatus according to claim 23, wherein said sealing means is positioned at the intersection of said cones.

25. Method for the collecting of a bacteriological or micro-biological or tissue specimen and the placing of said collected specimen in sealed, non-contaminating and non-debilitating environment while maintaining a sealed state of said environment comprising the steps of placing a sealed chamber means containing said environment and having a movable specimen collecting means passing therethrough in sealing relationship therewith adjacent the area from which said specimen is to be taken; collecting said specimen on said collecting means while said collecting means extends through said chamber means, retracting said collection means with said specimen into an air-lock like sealable zone which is before said chamber means and sealed from said environment; applying an additional sealing to said sealable zone to seal said collected specimen within said zone in a first sealed position; retracting said collection means with said collected specimen from said first sealed position into a second sealed position within said sealed chamber means; and placing said collected specimen in contact with at least one specimen medium in said environment.

26. Method according to claim 25 wherein said specimen medium is at least one transport type medium to maintain the condition of the collected specimen in transport to a laboratory.

27. Method according to claim 25 wherein said specimen medium is at least one culture type medium upon which at least a portion of said collected specimen is placed.

28. Method for the collecting of a bacteriological or mirco-biological or tissue specimen and the placing of said collected specimen in a sealed, non-contaminating and non-debilitating environment by maintaining a sealed state of said environment, said environment being within a sealed chamber means and having a movable specimen collecting means passing therethrough in sealing relationship therewith; there being an element extending from said sealed chamber around said collecting means to protect said collecting means and collected specimen from passage through ambient air after taking said specimen; comprising, positioning said element in an area from which said specimen is to be taken; extending said collecting means through and from said chamber means and from said element to collect said specimen; retracting said collection means with said specimen through said element into an air-lock type sealable zone which is before said chamber means and sealed from said environment; applying an additional sealing to said sealable zone to seal said collectied specimen within said zone in a first sealed position; retracting said collection means with said collected specimen from said first sealed position into a second sealed position within said environment; placing said collected specimen in contact with at least one specimen medium in said environment; and removing said protective element.

29. Method according to claim 28 wherein said protective element is removed after the step of applying said additional sealing.

30. Method according to claim 28 wherein said specimen medium is at least one transport type medium to maintain the condition of the collected specimen during transport to a laboratory.

31. Method according to claim 28 wherein said specimen medium is at least one culture type medium upon which at least a portion of said collected specimen is placed.

32. Method for the collecting of a bacteriological or micro-biological or tissue specimen and the placing of said collected specimen in a sealed, non-contaminating and non-debilitating environment by maintaining a sealed state of said environment, said environment being within a chamber means containing said environment in a sealed state and having movable specimen collecting means passing therethrough in sealing relationship therewith; there being an element having a closed end and extending from said sealed chamber around said collecting means to enclose and protect said collecting means from passage through ambient air prior to and after taking said specimen; comprising inserting a closed protective element into said specimen area; extending said collecting means from said sealed chamber means through said protective element to open said closed end; extending said collecting means through said open end to collect said specimen; collecting said specimen on said collecting means; withdrawing said collected specimen into said protective element until said end is closed; withdrawing said closed protective element from said specimen area; retracting said collection means with said specimen through said element into an air-lock like sealable zone which is before said chamber means and sealed from said environment; applying an additional sealing to said sealable to seal said collected specimen within said zone in a first sealed position; retracting said collection means with collected specimen from said first sealed position into a second sealed position within said environment; placing said collected specimen in contact with at least one specimen medium in said environment and removing said protective element and closed end.

33. Method according to claim 32 wherein said protective element and closed end is removed after the step of applying said additional sealing.

34. Method according to claim 32 wherein said specimen medium is at least one transport type medium to maintain the condition of the collected specimen during transport to a laboratory.

35. Method according to claim 32 wherein said specimen medium is at least one culture type medium upon which at least a portion of said collected specimen is placed.

36. Method according to claim 32 wherein said closed protective element is removed from said specimen area after said collected specimen is sealed within said zone in a first sealed position.

37. Method for the collecting of the bacteriological or microbiological or tissue specimen and placing said collected specimen in a non-contaminating and non-dibilitating specimen maintenance environment placing in a sealed chamber while maintaining the sealed state of said chamber, comprising the steps of: placing sealed chamber means containing said environment and having a movable specimen collecting means passing therethru in sealing relationship therewith adjacent an area from which said specimen is to be taken; collecting said specimen on said collecting means while said specimen collecting means extends through said chamber means withdrawing said collection means with said specimen into a sealable zone within said sealed chamber means; applying an additional sealing to said sealable zone to seal said collected specimen within said zone in a first sealed position; retracting said collection means with said collected specimen from said first sealed position into a second sealed position within said environment; and placing said collected specimen in contact with at least one specimen medium in said environment.

38. Method according to claim 37 wherein said collecting means is protected from passing thru ambient air before and after said specimen has been collected by an element extending from said sealed chamber means around said collecting means; additionally comprising positioning said element in said area from which said specimen is to be taken; extending said collecting means from said element to collect said specimen; retracting said collected specimen thru said element into said first sealable zone; applying an additional sealing to said sealable zone to seal said collected specimen within said zone in a first sealed position; withdrawing said sealed chamber means from said specimen area; retracting said collection means with said collected specimen from said first sealed position into a second sealed position within said environment; and placing said collected specimen in contact with at least one specimen medium in said environment.

39. An apparatus for collecting a bacteriological or microbiological or tissue specimen comprising:
   an elongated, hollow body member having one end open and the opposite end having an end wall with an orifice therein and having a tubular member extending interiorly from said wall coaxial with said orifice;
   a closure cap for said open end having a passageway therethrough coaxial with said orifice in said opposite end with first sealing means in said passageway;
   second sealing means on the tubular member of said opposite end;
   an elongated specimen collecting rod slidingly positionable within said body member through said passageway and said opposite end and cooperating with said first and second sealing members to form a sealed state within said body member, said rod being extensible from and retractable into said body member through said opposite end;
   and movable valve cap means positioned over said opposite end of said body member to close and seal the orifice in said opposite end when said rod is withdrawn into said body member.

40. The apparatus according to claim 39 further comprising an elongated protective tube removably positioned in a projection on said valve cap means on the axis of movement of said rod and encompa-sing said rod.

41. The apparatus according to claim 40 further comprising means to close the end of said tube opposite said projection.

42. The apparatus according to claim 39 wherein said diminished opening comprises a tubular member extending inwardly into said body member to receive said rod, said second sealing means being positioned interiorly of said tubular member at its inner most end, said sealing means and said valve cap forming a sealing zone when said specimen is withdrawn into said tubular member.

43. The apparatus according to claim 39 further comprising means positioned within said sealed body member to maintain the collected specimen after it is brought into said body member through said diminished opening.

44. The apparatus according to claim 39 wherein said valve cap is rotatable about said body member when said rod is withdrawn into said diminished opening.

45. A self-contained apparatus for collecting a bacteriological or microbiological or tissue specimen and maintaining said specimen comprising:
   chamber means having longitudinally opposing end portions with sealing means on each end portion and containing therein a non-contaminating specimen maintenance environment;
   additional closure and sealing means spacedly positioned outwardly and longitudinally of the sealing means on one of said end portion of said chamber means and cooperating with the sealing means on said one end portion to form a sealable air-lock at said one end portion of said chamber means for controlling passage of exterior atmosphere into said chamber, means through said one end portion; and
   specimen collecting means movably positioned through said chamber means, each of said end portion sealing means and said air-lock in sealing relationship with said chamber means and said end portion sealing means to form a sealed chamber interior and for extension therefrom to collect said specimen and for retraction thereinto to cooperatively allow entry of said collected specimen into said air-lock and into said sealed chamber interior while maintaining said sealed state of said chamber interior.

46. A self-containing apparatus for collecting a bacteriological or microbiological or tissue specimen and maintaining said specimen comprising:
   chamber means having longitudinally opposing end portions with sealing means on each and containing therein a non-contaminating specimen maintenance environment;
   additional closure and sealing means spacedly positioned outwardly and longitudinally of the sealing means on one of said end portion of said chamber means and cooperating with the sealing means on said one end portion to form a sealable air-lock at said one end portion of said chamber means for controlling passage of exterior atmosphere into said chamber means through said one end portion;
   specimen collecting means movably positioned through said chamber means, each of said end portion sealing means and said air-lock in sealing relationship with said chamber means and said end portion sealing means to form a sealed chamber interior and for extension therefrom to collect said specimen and for retraction thereinto to cooperatively allow entry of said collected specimen into said air-lock and into said sealed chamber interior while maintaining said sealed state of said chamber interior; and
   removable tubular means extending from said closure and sealing means and encompassing that portion of said specimen collecting means extending from said closure and sealing means to prevent passage of said collected specimen through ambient atmosphere.

47. A self-contained apparatus for collecting bacteriological or microbiological or tissue specimen and maintaining said specimen comprising:
   chamber means having opposing end portions with sealing means on each portion and containing therein a non-contaminating and non-debilitating specimen maintenance media environment for said specimen; a movable specimen collecting means positioned through said chamber means and each said sealing means in sealing relationship with said sealing means to form a sealed chamber interior and for extending from one end portion of said chamber means to collect said specimen and for retraction with said specimen through said one end into said chamber means; and an additional sealing means on said one end portion having an orifice therethrough to cooperate in coaxial relationship with an orifice in said one end portion through which said specimen collecting means traverses when said additional sealing means is in an open position and which orifice has a closed position to close and seal said one end portion after said retraction to maintain the seal of said chamber means, said additional sealing means being outward of the sealing means of said end portion and longitudinal thereof.

* * * * *